US011071484B2

(12) United States Patent
Eda et al.

(10) Patent No.: US 11,071,484 B2
(45) Date of Patent: Jul. 27, 2021

(54) REDUCE ELECTROMAGNETIC FREQUENCY EMISSIONS FROM A MOBILE DEVICE (71) Applicant: International Business Machines Corporation, Armonk, NY (US)

(72) Inventors: Sasikanth Eda, Vijayawada (IN); Abhishek Jain, Baraut (IN); Sandeep Ramesh Patil, Pune (IN); Manojkiran Eda, Vijayawada (IN)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/689,499

(22) Filed: Nov. 20, 2019

(65) Prior Publication Data

US 2021/0145339 A1    May 20, 2021

(51) Int. Cl.
*H04W 36/24* (2009.01)
*H04W 24/02* (2009.01)
*H04W 36/22* (2009.01)
*A61B 5/16* (2006.01)
*H04W 36/26* (2009.01)

(52) U.S. Cl.
CPC .............. *A61B 5/165* (2013.01); *H04W 24/02* (2013.01); *H04W 36/245* (2013.01); *H04W 36/26* (2013.01)

(58) Field of Classification Search
CPC .... A61B 5/165; H04W 36/245; H04W 24/02; H04W 36/26
USPC ......................................................... 455/436
See application file for complete search history.

(56) References Cited

U.S. PATENT DOCUMENTS

| 8,442,533 | B2 | 5/2013 | Neubacher | |
|---|---|---|---|---|
| 2013/0031190 | A1* | 1/2013 | Chan | G06Q 50/01 709/206 |
| 2013/0225194 | A1* | 8/2013 | Sung | H04W 72/082 455/452.2 |
| 2014/0232557 | A1* | 8/2014 | Harper | A61B 5/14532 340/870.16 |
| 2014/0362829 | A1* | 12/2014 | Kazmi | H04L 63/0442 370/332 |

(Continued)

OTHER PUBLICATIONS

Alharthi, "Context—Aware Stress Prediction System," Thesis for Faculty of Graduate and Postdoctoral Studies, Canada, 2016, 86 pages, https://pdfs.semanticscholar.org/6615/6d8374286bc2f82659fe81a03d85d990fb04.pdf.

(Continued)

*Primary Examiner* — Inder P Mehra
(74) *Attorney, Agent, or Firm* — Peter Edwards (57) ABSTRACT A method, system, and computer program product for limiting the amount of electromagnetic frequency emissions from a mobile device in a time of high anxiety. The method may include determining whether a user is awaiting a first notification on a mobile device. The method may also include estimating an anxiety level of the user based on the determining. The method may also include determining whether the anxiety level is above a threshold anxiety level. The method may also include calculating, in response to determining that the anxiety level is above the threshold anxiety level, a ping-pong rate for the mobile device. The method may also include reducing the ping-pong rate.

20 Claims, 7 Drawing Sheets

(56) References Cited

U.S. PATENT DOCUMENTS

| | | | |
|---|---|---|---|
| 2015/0229888 A1* | 8/2015 | Harada | A61B 5/6898 |
| | | | 348/207.1 |
| 2015/0324871 A1* | 11/2015 | Beloglazov | G06Q 30/0282 |
| | | | 705/347 |
| 2015/0332565 A1 | 11/2015 | Cho et al. | |
| 2016/0078430 A1* | 3/2016 | Douglas | H04L 63/08 |
| | | | 705/43 |
| 2016/0210578 A1* | 7/2016 | Raleigh | H04M 15/80 |
| 2017/0235357 A1* | 8/2017 | Leung | G06F 1/3265 |
| | | | 713/310 |
| 2018/0068573 A1 | 3/2018 | dos Reis Costa et al. | |
| 2018/0211112 A1* | 7/2018 | Asbun | G06F 3/013 |
| 2019/0385749 A1* | 12/2019 | Dohrmann | G16H 20/60 |
| 2020/0125311 A1* | 4/2020 | Nakayama | H02J 7/007192 |

OTHER PUBLICATIONS

Kruger et al., "High Ringxiety: Attachment Anxiety Predicts Experiences of Phantom Cell Phone Ringing," Cyberpsychology, Behavior, and Social Networking, vol. 19, No. 1, 2016, 5 pages, DOI: 10.1089/cyber.2015.0406, https://deepblue.lib.umich.edu/bitstream/handle/2027.42/140350/cyber.2015.0406.pdf?sequence=1&isAllowed=y).

Henderson, "Phantom vibration syndrome: Up to 90 per cent of people suffer phenomenon while mobile phone is in pocket," Independent, Jan. 10, 2016, 3 pages, https://www.independent.co.uk/life-style/health-and-families/health-news/phantom-vibration-syndrome-up-to-90-per-cent-of-people-suffer-phenomenon-while-mobile-phone-is-in-a6804631.html.

* cited by examiner

REDUCE ELECTROMAGNETIC FREQUENCY EMISSIONS FROM A MOBILE DEVICE

BACKGROUND

The present disclosure relates to ping-pong rates and electromagnetic frequency emissions, and more specifically to limiting an amount of electromagnetic frequency emissions from a mobile device in times of high anxiety.

When a mobile device communicates with a cell tower, there may be a signal strength between the device and the cell tower. The signal strength may correspond to the distance between the device and the cell tower, in some instances. If the signal strength is weak (for example, because there is a large distance between the mobile device and the cell tower) then a handover, or hand-off, of the mobile device from the current cell tower to a next cell tower (for example, adjacent to the current cell tower) is performed. This is called a handover. In some instances, after a connection is established between a mobile device and a cell tower (even if the connection is strong), the mobile device is handed back to the original cell tower due to workload distribution, native migrations, etc., resulting in a ping-pong handover. The mobile device may continue to bounce back and forth, or ping-pong, between two cell towers.

SUMMARY

The present disclosure provides a computer-implemented method, system, and computer program product to limit an amount of electromagnetic frequency emissions from a mobile device in times of high anxiety. The method may include determining whether a user is awaiting a first notification on a mobile device. The method may also include estimating an anxiety level of the user based on the determining. The method may also include determining whether the anxiety level is above a threshold anxiety level. The method may also include, calculating in response to determining that the anxiety level is above the threshold anxiety level, a ping-pong rate for the mobile device. The method may also include reducing the ping-pong rate. The system and computer program product may include similar steps.

The above summary is not intended to describe each illustrated embodiment or every implementation of the present disclosure.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present disclosure relates to ping-pong rates and electromagnetic frequency emissions, and more specifically to limiting an amount of electromagnetic frequency emissions from a mobile device in times of high anxiety. While the present disclosure is not necessarily limited to such applications, various aspects of the disclosure may be appreciated through a discussion of various examples using this context.

Ping-pong handover may occur when a mobile device bounces back and forth, or ping-pongs, between cell towers. Each connection between the mobile device and a cell tower may cause a small magnetic discharge (i.e., electromagnetic frequency emission). In some instances, a user of the mobile device may mistake the magnetic discharge, or electromagnetic frequency emissions, for a mobile phone vibration (for instance, indicating a notification on the mobile device). Mistakenly believing that one's mobile phone is vibrating may be referred to as phantom vibration syndrome, and these magnetic discharges may be a common cause of the syndrome.

For example, electromagnetic frequency (EMF) emissions may cause nerve impulses in a user, and at times of increased anxiety, particularly when the anxiety is due to a pending notification, a user may be able to feel these impulses. Anxiety may refer to feelings of worry, fear, and/or nervousness, typically accompanied by an increased heart rate, along with possible other physical symptoms. When anxiety increases, a user may experience heightened senses and/or sensitivity, particularly towards the cause of the anxiety. When a user is expecting a notification on their mobile device, for instance, the anxiety towards their pending notification may result in a heightened sensitivity/awareness of the mobile device. Therefore, the user may be more aware of sensations from the mobile device and may be more likely to sense the nerve impulses from the EMF emissions. In other words, the user may be more likely to consciously notice sensations from the mobile device that the user may otherwise unconsciously ignore.

These mistaken magnetic discharges may result in draining of the mobile device's battery (for example, due to a user waking up their mobile device to check for notifications) and/or increased application synchronizations/downloads (for example, due to a user more frequently switching on and off from airplane mode and/or Wi-Fi to check for notifications) which may also lead to battery draining.

In some instances, particularly in situations of increased anxiety, a user may be more likely to anticipate signals, or notifications, from their mobile device (for example, a user may be nervously waiting for a particular notification) and may mistake the magnetic discharges/electromagnetic frequency emissions (for example, due to phantom vibration syndrome) for his or her anticipated signals, or notifications. For example, an individual may have completed a telephonic interview, and, at the end of the interview, was told to expect a call in an hour. In this example, the individual may have an increased anxiety due to the important pending phone call and may be more prone to mistake magnetic discharges for vibrations associated with the phone call. This may result in an increased frequency of checking the mobile device and draining of the mobile device battery.

The present disclosure provides a computer-implemented method, system, and computer program product to limit/reduce an amount of electromagnetic frequency emissions from a mobile device in times of high anxiety. Limiting, or reducing, magnetic discharge from a mobile device, particularly when a user may have increased anxiety, may help prevent increased checking of the mobile device, and may reduce battery drainage of the mobile device. Anxiety levels of a user of a mobile device may be determined, or estimated, based on at least whether the user is expecting a notification in the relatively near future (e.g., the next hour, the next two hours, the next three hours, etc.). For example, a user expecting a notification in the next few hours may have a relatively large increase in anxiety where a user expecting a notification in a week may have minimal to no increase in anxiety.

If it is determined that a user has an increased anxiety, the rate of electromagnetic frequency (EMF) signals transmitted to the cell tower may be reduced using cognitive radio. Cognitive radio is intelligent radio-transceiver hardware that can dynamically change transmission and/or reception parameters. Further, cognitive radio is able to configure radio/system parameters such as frequency. Through cognitive radio capabilities, the EMF signals may be adjusted. Decreasing the rate of EMF signals may decrease the power of the radio waves to the tower. This rate of EMF signals/emissions transmitted to the cell tower may be referred to herein as a ping-pong rate. The higher the ping-pong rate, the more chance a user may feel/register the magnetic discharge from the ping-pong between cell towers in times of increased anxiety.

In some instances, a higher ping-pong rate may cause more ping-pong between the mobile device and the cell tower. A higher ping-pong rate may correspond to higher-power radio waves emitted from the mobile device. Conventionally, when a mobile device is moving away from one cell tower and towards the other, the mobile device is transferred to the other cell tower to maintain connection/signal between the mobile device and a tower. When the mobile device has higher power radio waves, the mobile device may maintain a strong connection with the cell tower even when moving toward another cell tower, which it may also be able to connect with. This may cause the signal to go back and forth (i.e., ping-pong) between the two towers. Therefore, a higher ping-pong rate may result in a greater chance for the mobile device to ping-pong between cell towers, in some instances.

In some instances, the power of the transmitted EMF signals from the mobile device, which may correspond to the rate of EMF emissions, may be controlled depending on the connection (e.g., signal strength) to the cell tower. The higher the power of the transmitted EMF signals, the quicker the battery life of the mobile device may be drained. When signal strength of a cell tower is strong, less EMF signal power may be needed for the cell tower to receive a clear signal from the mobile device. Therefore, the rate of EMF signals may be reduced in order to preserve battery life of the mobile device. Reducing the rate of EMF signals/emissions (i.e., ping-pong rate) from the mobile device may reduce the chance that a user may feel the magnetic discharge from the emissions, because the reduced rate may be undetectable (or at least less detectable) by a user. Further, as discussed above, reducing the rate of EMF signals/emissions from the mobile device may reduce the chances of ping-pong between cell towers.

Figure 1:
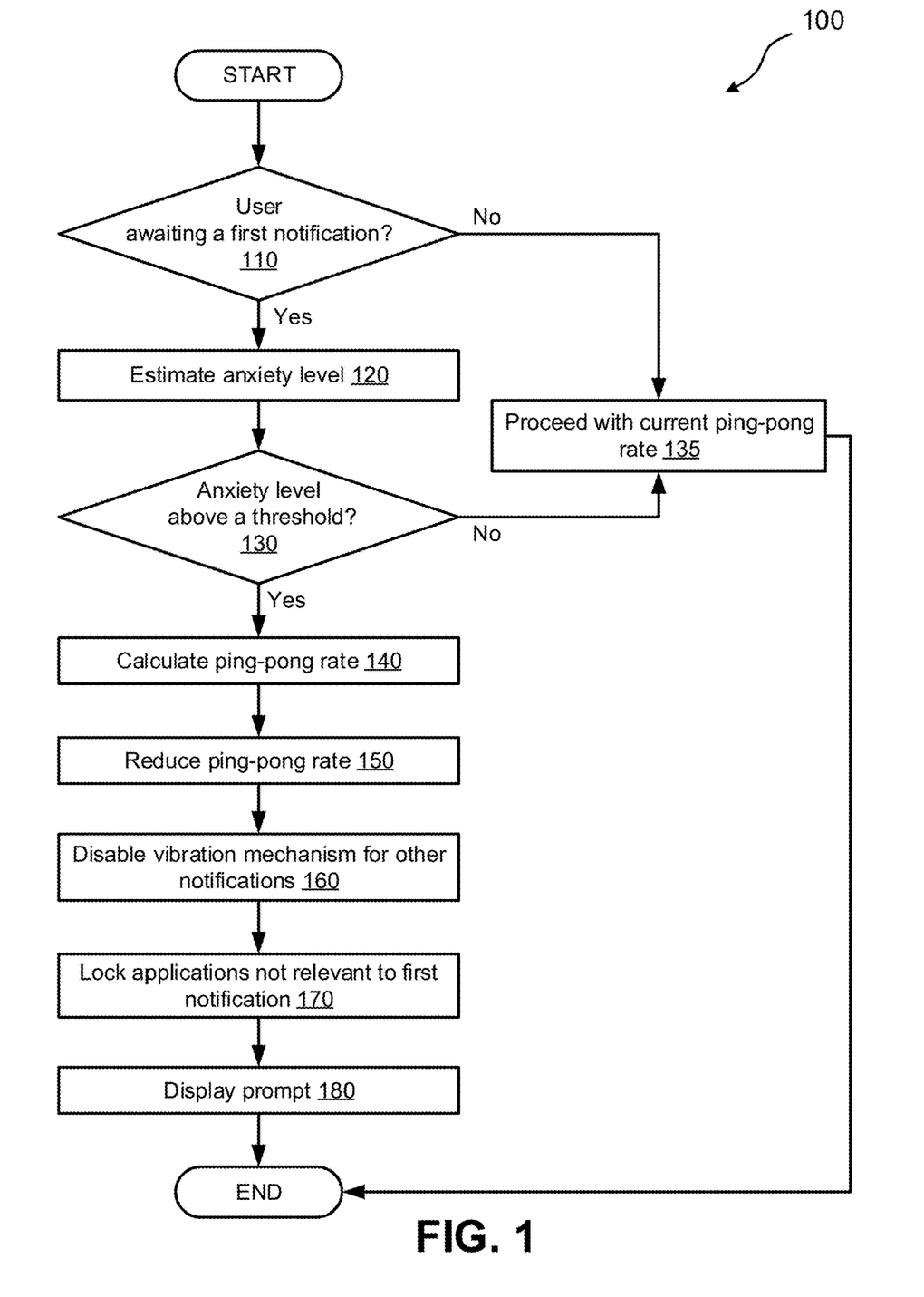
FIG. 1 depicts a flowchart of a set of operations for limiting an amount of electromagnetic frequency emissions, according to some embodiments.

Referring now to FIG. 1, a flowchart illustrating a method 100 for limiting an amount of electromagnetic frequency emissions from a mobile device is depicted, according to some embodiments. In some embodiments, method 100 is executed by a server (e.g., computer system/server 502 (FIG. 5) on, or connected to, a mobile device (e.g., mobile device 320 (FIG. 3) and/or mobile device 410 (FIG. 4)). In some embodiments, the method 100 is implemented as a computer script or computer program (e.g., computer executable code) to be executed on or connected to a computer system (e.g., computer system 500 (FIG. 5)). In some embodiments, the computer system is on or connected to the mobile device. In some embodiments, the mobile device is within a cloud computing environment (e.g., cloud computing environment 50 (FIG. 6)).

Method 100 includes operation 110 to determine whether a user is awaiting a first notification, or, in some instances, multiple notifications. As discussed herein, a pending, or expected, notification may increase the anxiety of a user. A user with increased anxiety may be more likely to mistake EMF emissions from a mobile device as an indication of a received notification (for example, via mobile phone vibration).

In some embodiments, various data from the mobile device, particularly data relating to communication applications (e.g., messaging applications, email applications, phone call applications, etc.) is analyzed for information to determine whether the user is awaiting a notification. For example, data from a messaging application may be analyzed to determine whether, in any messages, there was any discussion of future contact/notifications. In these embodiments it may be beneficial that no data is accessed/analyzed without permission from the user. For example, in some embodiments, a user may have to opt in to method 100 and may be able to opt out at any time. In some embodiments, a user can opt in, or select, various features and can opt out of other features—customizing what information is used and what actions are taken with the selected information. In some embodiments, a user receives a prompt allowing for selection of data that the user would like used/analyzed when executing method 100.

In some embodiments, any personal data may be encrypted and anonymized before it is analyzed, therefore protecting the identity of the user. In some embodiments, any features discussed in operation 110 and/or method 100 may be turned off when not actively being used, therefore preventing any overuse or unnecessary control of personal data and the mobile device. Determining whether a user is awaiting a notification is discussed further in FIG. 2.

If it is determined that a user is not awaiting any notifications, method 100 proceeds to operation 135 to proceed with the current ping-pong rate. If a user is not awaiting a notification, the user is less likely to have an increase in anxiety, and is less likely to mistake a small magnetic discharge (i.e., EMF emissions) for a mobile device vibration. Therefore, the mobile device is less at risk for increased battery drainage and the mobile device may maintain its current ping-pong rate.

If it is determined that a user is awaiting at least the first notification, method 100 proceeds to operation 120 to estimate an anxiety level of the user. This determination may be based, in part, on the fact that the user is awaiting notification, but further information may be available in some embodiments. For example, the mobile device may be connected to one or more health devices. In these embodiments, it may be beneficial to prevent health devices and their corresponding data from being accessed without user permission (for example, via prompt, opt in/opt out, customization of which features are being used, encryption of personal data, etc.). In some embodiments, one or more health devices are a part of the mobile device. Health devices, as referred to herein, may be devices that help indicate a health level and anxiety level of the user. In some embodiments, the health devices include at least a heart rate monitor. An increased heart rate may correspond to an increase in anxiety. In some embodiments, the health devices include a fitness tracker (e.g., a step tracker). The fitness tracker may help determine a cause of the increase in heart rate. For instance, if the fitness tracker indicates that the user is currently active (e.g., steps are increasing), an increase in heart rate may be determined to be because of the increase in activity as opposed to an anxiety induced heart rate increase.

In some embodiments, estimating an anxiety level of the user includes determining an importance of the first notification to the user in relation to their anxiety. The importance of the first notification may be determined by analyzing user data (that the user has granted permission to be accessed) and determining user priorities based on the analyzing. For example, if a user is currently unemployed, an email, phone call, etc. regarding a job interview may have a high importance and may have a high impact on the user's anxiety. In another example, if a user is currently employed, a notification regarding a small bonus may not have as high of an importance and may not affect the user's anxiety. In another example, a user may have given permission for their calendar data to be analyzed/used. In this example, it may be determined that the user is getting married in a month. With an upcoming wedding, a notification regarding a raise or bonus may be determined to have a high importance and a relatively high impact on the user's anxiety.

In some embodiments, estimating an anxiety level of the user includes determining the potential effects of the first notification. For instance, determining whether the first notification may cause a chain of events/actions in response to the notification. A notification causing a chain of actions/events may result in a higher anxiety level than those that do not cause a chain of actions/events. For example, a notification indicating that a student failed all their college courses for the semester may cause the student to transfer colleges, triggering emails/communications to admissions offices, requests for bank loans, relocation, etc. This may cause high anxiety. In another example, a student may receive a notification that they got all A's in their classes for the semester. In this example, the notification may cause the student to go out for a celebratory dinner, but may not cause any other actions. This may cause minimal anxiety in the user.

In some embodiments, a plurality of factors (e.g., health devices, importance of the notification, potential effects of the notification, etc.) are weighted in order to determine the anxiety level of the user.

In some embodiments, further information beyond the fact that the user is awaiting notification may not be available. In these embodiments, estimating may be based on the determining from operation 110. For instance, if a user is awaiting a notification, it may be more likely that the user has a higher anxiety level than if the user was not awaiting a notification. Estimating an anxiety level of the user is further discussed in FIG. 3.

Method 100 includes operation 130 to determine whether the anxiety level is above a threshold anxiety level. In some embodiments, the threshold anxiety level is predetermined by the user. In some embodiments, the threshold anxiety level is calculated (for example, using an algorithm such as a machine learning algorithm). In some instances, past health data gathered from the health devices may be used to determine the threshold anxiety level. In some embodiments, the threshold anxiety level is determined based on statistics, information, and or studies published through medical organizations. The statistics and information may be location based, in some instances. For example, a user living in New York may have different standard anxiety levels than someone living in Iowa. Therefore, the medical organization publications used may be publications from a certain area (e.g., a surrounding area of the user). Determining whether the anxiety level is above a threshold anxiety level is further discussed in FIG. 3.

If it is determined that the anxiety level is not above the threshold anxiety level, method 100 proceeds to operation 135 to proceed with the current ping-pong rate, discussed herein. Because the user does not have an anxiety level above a threshold, the user may not be as anxious and may be less likely to mistake a small magnetic discharge (i.e., EMF emissions) for a mobile device vibration. Therefore, the mobile device may not be at risk for increased battery drainage and the mobile device may maintain its current ping-pong rate.

If it is determined that the anxiety level is above a threshold anxiety level, method 100 proceeds to operation 140 to calculate a ping-pong rate from the mobile device. In some embodiments, the ping-pong rate is calculated using cognitive radio. Cognitive radio is intelligent radio-transceiver hardware that can configure various radio/signal parameters. Cognitive radio may be adaptive and may be able to monitor and modify its performance. In some embodiments, cognitive radio hardware is built into (e.g., inside) the mobile device.

A cognitive radio algorithm may be used to calculate the ping-pong rate (i.e., the rate of EMF emissions transmitted from the mobile device at the current time). In some embodiments, the cognitive radio algorithm may utilize various radio/signal parameters (e.g., signal strength, transmission channels, etc.) for the calculation.

Method 100 includes operation 150 to reduce the ping-pong rate. The ping-pong rate may be reduced using cognitive radio and the cognitive radio algorithm. As discussed herein, cognitive radio may configure various radio/signal parameters. In some embodiments, the emissions may be reduced by a predetermined amount/strength. In some embodiments, the cognitive radio algorithm determines a reduction amount. The ping-pong rate may be reduced such that the power of radio waves decreases, but the connection to the cell tower is maintained.

In some embodiments, reducing the ping-pong rate may include communicating the new ping-pong rate to a base station of the current cell tower. In some embodiments, the base station is part of the cell tower. In some embodiments, the base station is connected to the cell tower. The base station may control ping-pong handover and may keep the session (e.g., connection) between the mobile device and the cell tower alive. Communicating the new ping-pong rate to the base station may help ensure that the rate of EMF emissions from the base station to the mobile device is the ping-pong rate. Therefore, any magnetic discharge from the mobile device due to signals sent from the base station may also be undetectable (or at least less detectable) to users, particularly in times of higher anxiety. In some embodiments, the base station is an Evolved Node B (eNodeB). eNodeB may be a base station used in Long-Term Evolution (LTE) networks.

In some embodiments, reducing the ping-pong rate includes determining that a cell tower (currently connected to the mobile device) has a signal strength greater than a threshold strength. The threshold strength may be a signal strength of the cell tower at which the cell tower is able to maintain connectivity between the mobile device and the cell tower. In other words, the threshold strength may indicate a necessary signal strength to maintain connectivity between the mobile device and the cell tower. If the user is awaiting a notification, a user may want to reduce/eliminate any risk of missing their notification due to loss of connectivity to the cell tower. Thus, the user may wish to avoid reducing the ping-pong rate to a degree that reduces the signal strength below that signal strength. By determining that the signal strength of the cell tower is above the threshold strength, it may be determined that reducing the ping-pong rate will not affect (e.g., lose) the connectivity between the mobile device and the cell tower. In some embodiments, the signal strength corresponds to a distance between the device and the cell tower. For example, if the mobile device is a farther distance from the connected cell tower, the signal strength from that cell tower may be weak. In some embodiments, the threshold strength is determined using cognitive radio.

In some embodiments, reducing the ping-pong rate of the EMF emissions further includes, in response to determining that the cell tower has a signal strength greater than the threshold strength, decreasing a power of electromagnetic frequency emissions transmitted from the mobile device. This way, the ping-pong rate and power of EMF emissions is only decreased after checking whether the decrease will result in losing connection with the cell tower (for example, due to weak signal strength). By determining whether the cell tower has a signal strength greater than the threshold strength before decreasing the power of EMF emissions, it may be ensured that reducing the ping-pong rate will not cause the connection between the cell tower and the mobile device to be lost. When a user is awaiting a notification (e.g., a phone call about a job) it may be crucial to maintain the connection in order to ensure that the user receives their awaited notification.

In some embodiments, once the ping-pong rate has been reduced, method 100 includes disabling a vibration alert mechanism for any incoming notifications but the first notification (in operation 160). For example, if a user is awaiting a call about a job interview, the vibration alert mechanism for all other notifications (e.g., text messages, emails, etc.) may be disabled so that the mobile device will only vibrate for incoming calls from the interviewer. This may help prevent an increased checking of the mobile device when awaiting the notification, which may help preserve the battery of the mobile device.

In some embodiments, once the first notification (i.e., the awaited notification) has been received, the vibration alert mechanism may be reinstated for all notifications. Reinstating the vibration alert mechanism may help prevent the user from missing too many notifications. The user may only miss alerts for other notifications while awaiting the notification, once the awaited notification has been received, the user may again receive alerts (for instance, through mobile phone vibration) for all notifications.

In some embodiments, method 100 further includes locking applications that are not relevant to the first notification, in operation 170. Locking applications may prevent a user from accessing the locked applications. For example, if a user is awaiting an email, all other applications (such as applications involving games, text messaging, calling, calendar, music, etc.) may be locked so that a user cannot access them. Locking all other applications may help prevent increased checking of the mobile device when awaiting the notification, which may help preserve the battery of the mobile device. Further, locking other applications may prevent notifications from being received from the other applications, which may help both the battery life of the mobile device and the anxiety of the user.

In some embodiments, method 100 includes operation 180 to display a prompt suggesting that the user change an orientation of the mobile device. In some instances, certain orientations of the mobile device may cause the user to more easily detect EMF emissions from the mobile device. For example, a mobile device oriented horizontally with a back of the device closest to the user may have EMF emissions more easily detected by the user, as the back of the device (which is closest to the user) is where the emissions are transmitted from. In this example, the mobile device may prompt the user to turn the mobile device horizontally and/or flip the mobile device so that the front of the device is closest to the user.

Figure 2:
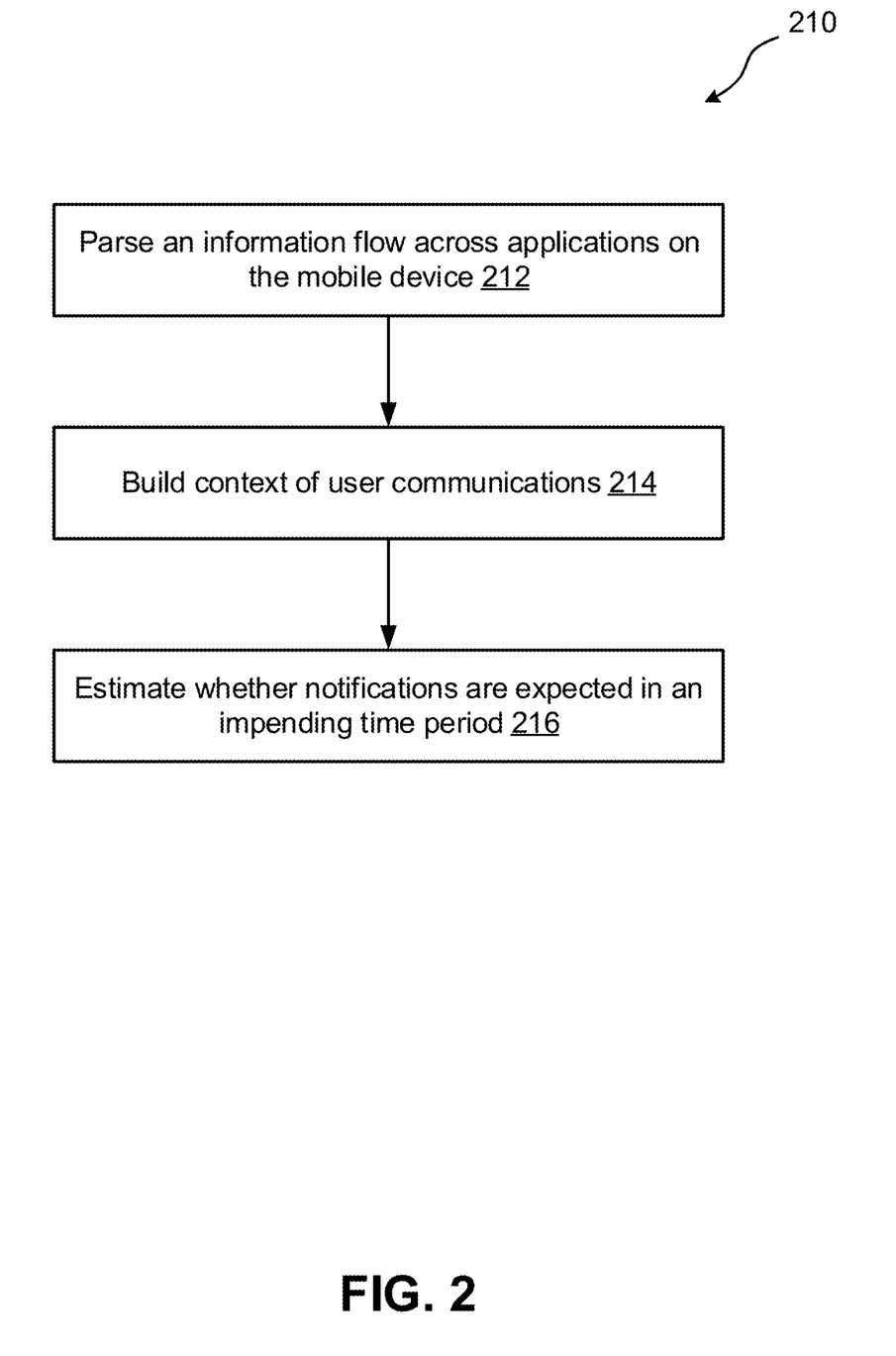
FIG. 2 depicts a flowchart of a set of operations for determining whether a user is awaiting a notification, according to some embodiments.

Referring to FIG. 2, a flowchart illustrating a method 210 for determining whether a user is awaiting a notification is depicted, according to some embodiments. In some embodiments, method 210 is executed by a server (e.g., computer system/server 502 (FIG. 5) on, or connected to, a mobile device (e.g., mobile device 320 (FIG. 3) and/or mobile device 410 (FIG. 4)). In some embodiments, the method 210 is implemented as a computer script or computer program (e.g., computer executable code) to be executed on or connected to a computer system (e.g., computer system 500 (FIG. 5)). In some embodiments, the computer system is on or connected to the mobile device. In some embodiments, the mobile device is within a cloud computing environment (e.g., cloud computing environment 50 (FIG. 6)). In some embodiments, method 210 corresponds to operation 110 (FIG. 1).

Method 210 includes operation 212 to parse an information flow across one or more applications on the mobile device. As discussed herein, in some embodiments, no information/data may be gathered/analyzed without being allowed/granted by the user. In some embodiments, the one or more applications include at least one of a messaging application, an email application, and a calendar application. The mobile device may use a parsing engine (e.g., parsing engine 330 (FIG. 3)) to parse/analyze (e.g., perform semantic and syntactic analysis) the data across the applications. In some embodiments, all applications on the mobile device are parsed. In some embodiments, a user gives permission for certain applications to be parsed, and all other applications without specific permissions are not parsed. In some embodiments, relevant applications may be identified, and only the relevant applications may be parsed. For example, communication applications (e.g., applications involving messaging, calling, email, calendar, etc.) may be determined to be relevant, where gaming applications may not be relevant. In some embodiments, the parsing engine is built within the operating system of the mobile device. In some embodiments, the parsing engine is downloaded as an application on the mobile device.

In some embodiments, determining whether a user is awaiting a notification includes identifying patterns of use of the user. Patterns of use may be repeated actions (of the user) on the mobile device. For example, a user may repeatedly and/or continuously open and close their email application every few minutes, refreshing their inbox while in the email application. This pattern may be identified as a pattern of use of the user. In another example, a user may repeatedly wake up and sleep their mobile device every five minutes.

Method 210 includes operation 214 to build context of user communications based on the parsing. Once the data/information has been parsed, the information may be combined/connected in order to get an indication of the user's potential upcoming notifications. For example, context may be built to indicate that a user had a job interview the previous day, and is expecting a notification with the results of the job interview. In another example, context may be built indicating that a user receives a call from their Grandmother every Wednesday at 7:00 PM. In some embodiments, building context of user communications is further based on the identified patterns of use of the user. In some instances, repeated actions of a user may indicate that the user is awaiting a notification. For example, the repeated opening and closing of an email application on the mobile device may indicate that a user is awaiting an email notification. If the user was awaiting the results of a job interview (discussed in the example above) and was also repeatedly opening and closing an email application, for example, context may be built to indicate that not only is the user awaiting a notification of the results, but that the notification the user is awaiting is an email.

Method 210 includes operation 216 to estimate whether notifications are expected in an impending time period, based on the building (in operation 214). Notifications that may cause anxiety in a user are likely notifications that are expected soon, or in a close future time period. For example, a notification that is not expected for another week is less likely to cause anxiety in a user than a notification expected within the next two hours. Therefore, an impending time period may be a time period close to the current time period. For example, the impending time period may be a time period a few hours away and/or within the next few hours (for example, one hour, two hours, three hours, etc.). In some embodiments, estimating whether notifications are expected in an impending time period may include determining whether the notification is expected within a certain time period and determining/calculating how close the certain time period is to the current time. If the certain time period is close to the current time, the notification may be expected in an impending time period.

Figure 3:
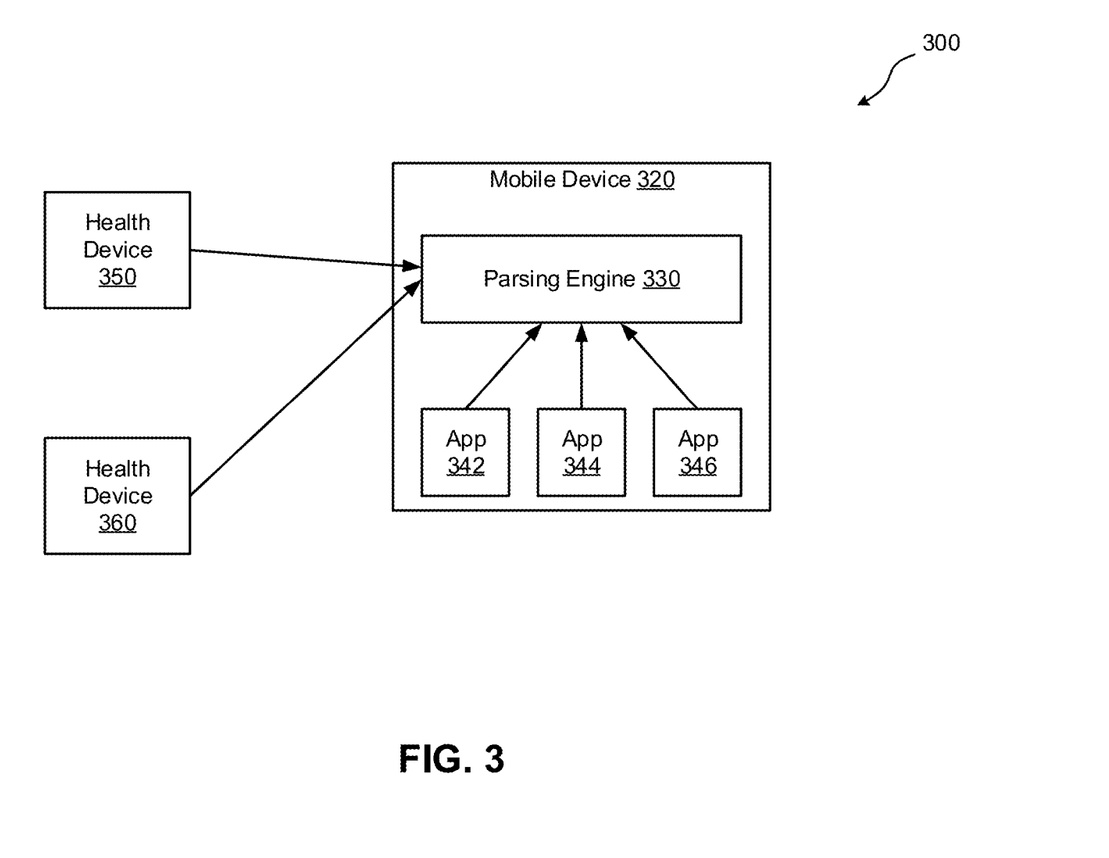
FIG. 3 depicts a block diagram of an example mobile device environment, according to some embodiments.

Referring to FIG. 3, a block diagram of an example mobile device environment 300 is depicted, according to some embodiments. Mobile device environment 300 includes a mobile device 320 and health devices 350 and 360. In some embodiments, the mobile device 320 is connected to one or more health devices. FIG. 3 depicts two health devices 350 and 360, but any number of health devices may be connected to mobile device 320. Health devices 350 and 360 may be connected to mobile device 320 through Internet of Things (IoT), a network, cloud computing (e.g., cloud computing environment 50 (FIG. 6), wireless internet, etc. In some embodiments, as depicted, the health devices 350 and 360 are separate but connected to mobile device 320. As discussed herein, in some embodiments, no data/information may be used without allowance or permission from the user.

In some embodiments, when mobile device 320 is connected to one or more health devices (e.g., health devices 350 and 360), estimating an anxiety level of the user may include collecting health data from the one or more health devices (e.g., health devices 350 and 360), analyzing the health data from the one or more health devices, and determining, based on the analyzing an approximation of the anxiety level of the user. As discussed herein, health devices include at least a heart rate monitor and may also include other devices such as a fitness tracker. For example, health device 350 may be a heart rate monitor and health device 360 may be a fitness tracker. In some embodiments, one or more of the health devices 350 and 360 are part of the mobile device 320 (not depicted).

In some embodiments, when the one or more health devices (e.g., 350 and 360) include a heart rate monitor, the health data may include a heart rate of the user and analyzing the health data may include determining whether the user's heart rate is escalated/increased, as an increased heart rate may correspond to an increase in anxiety.

In some embodiments, when the health devices (e.g., 350 and 360) also include a fitness tracker (e.g., a step tracker), the health data may include fitness data (e.g., step count, activity levels, etc.). Analyzing the health data may include analyzing the fitness data and, in cases of an increased heart rate, determining a cause of the increase. The fitness tracker may help determine a cause of the increase in heart rate. For instance, if the fitness tracker indicates that the user is currently active (e.g., steps are increasing), an increase in heart rate may be determined to be because of the increase in activity as opposed to an anxiety induced heart rate increase.

In some embodiments, when mobile device 320 is connected to one or more health devices (e.g., health devices 350 and 360), determining whether the anxiety level is above the threshold anxiety level may include collecting past health data from the one or more health devices in a past time period. Past health data may help establish baseline health levels of the user and analyzing the health/anxiety of the level may be more specific/customized to the user.

Determining whether the anxiety level is above a threshold anxiety level may further include determining, using the past health data, a threshold health level of the user. The threshold health level of the user may be a baseline, or resting, health level of the user. The past health data may be analyzed to establish a standard/average health level of the user. In some embodiments, a health level refers to the amounts/readings of data for the health devices. For example, a health level may be 70 bpm (from a heart rate monitor) and 200 steps per hour (from a step tracker).

Determining whether the anxiety level is above the threshold anxiety level may further include determining the threshold anxiety level of the user using the threshold health level. In some embodiments, the anxiety level refers to the amounts/readings of data from the health devices that corresponds to anxiety. For example, heart rate and step count may relate/correspond to anxiety (as discussed herein), whereas a calorie counter may not relate to anxiety. In some embodiments, anxiety level may be the level of anxiety (e.g., high, medium, low, etc.) of the user. The threshold anxiety level may be the anxiety level of the user when the user is at a threshold health level. In other words, it may be the baseline, or resting, anxiety level of the user.

Determining whether the anxiety level is above the threshold anxiety level may further include comparing the anxiety level (at the current time) to the threshold anxiety level. The current anxiety level of the user may be compared to the threshold anxiety level to determine whether the current anxiety level is higher than the threshold anxiety level. If so, the user may have an increase in anxiety.

In some embodiments, mobile device 320 includes parsing engine 330 and applications 342, 344, and 346. As discussed herein, the mobile device 320 may use a parsing engine 330 to parse/analyze (e.g., perform semantic and syntactic analysis) the data across the applications. The applications 342, 344, and 346 may transmit data to the parsing engine 330 and parsing engine 330 may perform sentiment analysis (for example) on the data.

Figure 4:
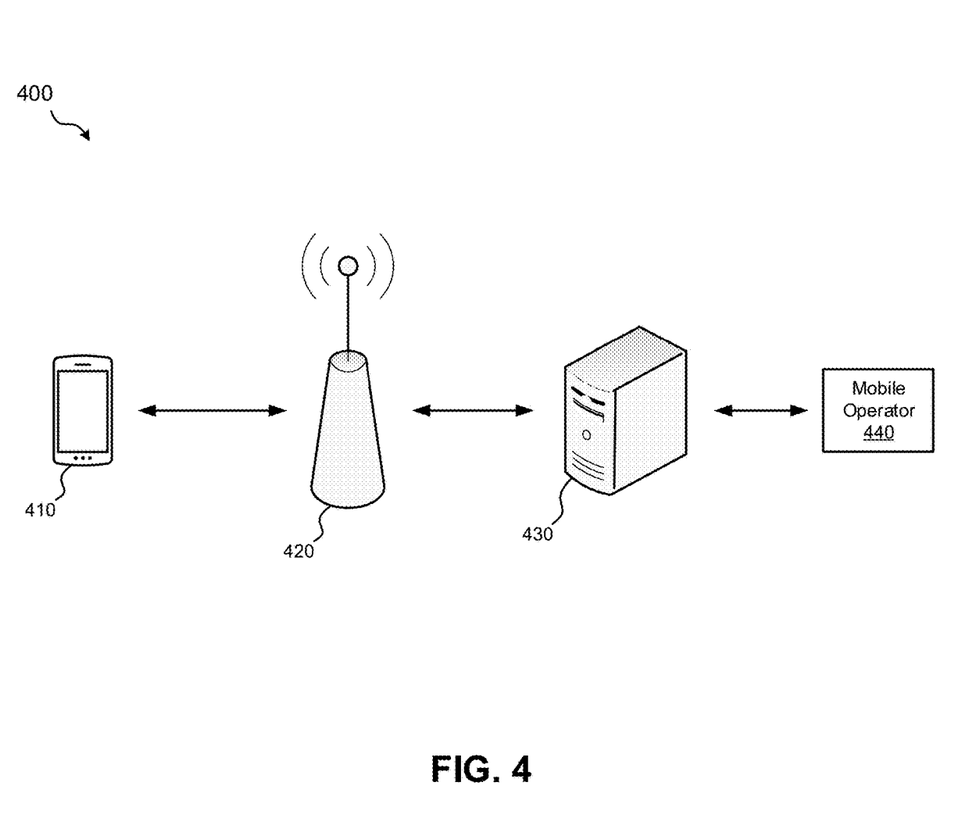
FIG. 4 depicts a schematic diagram of an example cognitive radio environment, according to some embodiments.

Referring to FIG. 4, a schematic diagram of an example cognitive radio environment 400 is depicted, according to some embodiments. Cognitive radio environment 400 includes a mobile device 410, a cell tower 420, a base transceiver station 430, and a mobile operator 440. The mobile device 410 may transmit EMF emissions to the cell tower 420, and the cell tower 420 may transmit EMF emissions back to the mobile device 410. Base transceiver station 430 may direct/facilitate communication between the mobile device 410 and a network. In some embodiments, base transceiver station 430 is part of cell tower 420. In some embodiments, as depicted in FIG. 4, base transceiver station 430 is separate but connected to cell tower 420. In some embodiments, base transceiver station 430 is an eNodeB. Mobile operator 440 may provide wireless communications services to the mobile device 410. In some embodiments, mobile operator 440 is a wireless service provider. In some embodiments, the mobile operator 440 controls the mobile device 410 communications with the cell tower 420 and the base transceiver station 430.

Figure 5:
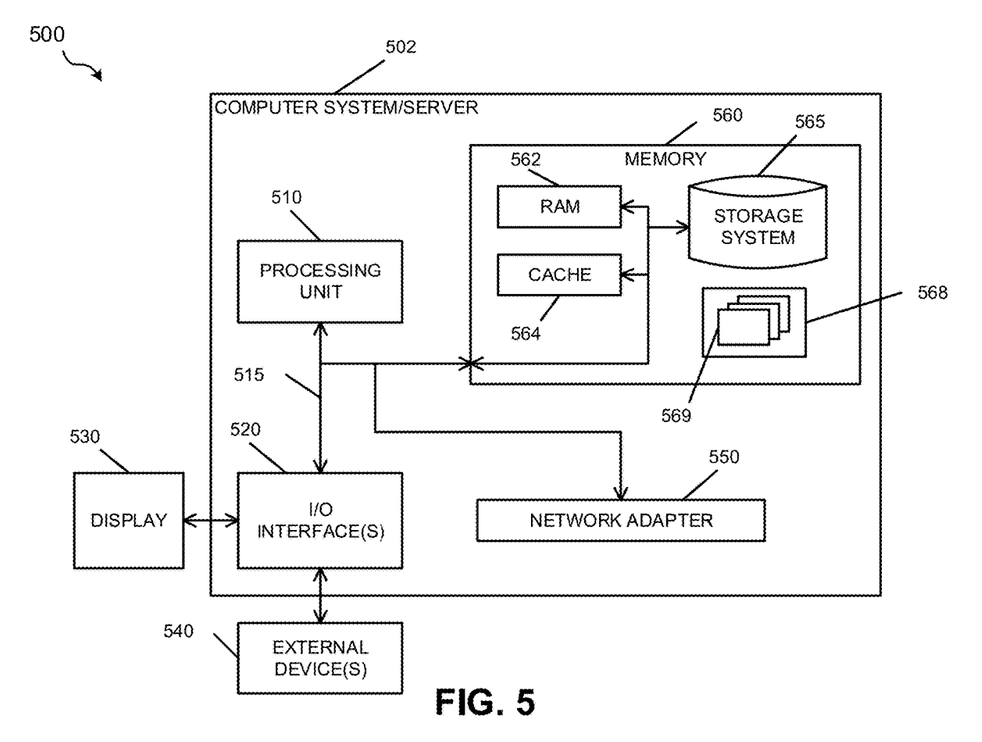
FIG. 5 depicts a block diagram of a sample computer system, according to some embodiments.

Referring to FIG. 5, computer system 500 is a computer system/server 502 is shown in the form of a general-purpose computing device, according to some embodiments. In some embodiments, computer system/server 502 is located on the linking device. In some embodiments, computer system 502 is connected to the linking device. The components of computer system/server 502 may include, but are not limited to, one or more processors or processing units 510, a system memory 560, and a bus 515 that couples various system components including system memory 560 to processor 510.

Bus 515 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 502 typically includes a variety of computer system readable media. Such media may be any available media that is accessible by computer system/server 502, and it includes both volatile and non-volatile media, removable and non-removable media.

System memory 560 can include computer system readable media in the form of volatile memory, such as random-access memory (RAM) 562 and/or cache memory 564. Computer system/server 502 may further include other removable/non-removable, volatile/non-volatile computer system storage media. By way of example only, storage system 565 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 515 by one or more data media interfaces. As will be further depicted and described below, memory 560 may include at least one program product having a set (e.g., at least one) of program modules that are configured to carry out the functions of embodiments of the disclosure.

Program/utility 568, having a set (at least one) of program modules 569, may be stored in memory 560 by way of example, and not limitation, as well as an operating system, one or more application programs, other program modules, and program data. Each of the operating system, one or more application programs, other program modules, and program data or some combination thereof, may include an implementation of a networking environment. Program modules 569 generally carry out the functions and/or methodologies of embodiments of the invention as described herein.

Computer system/server 502 may also communicate with one or more external devices 540 such as a keyboard, a pointing device, a display 530, etc.; one or more devices that enable a user to interact with computer system/server 502; and/or any devices (e.g., network card, modem, etc.) that enable computer system/server 502 to communicate with one or more other computing devices. Such communication can occur via Input/Output (I/O) interfaces 520. Still yet, computer system/server 502 can communicate with one or more networks such as a local area network (LAN), a general wide area network (WAN), and/or a public network (e.g., the Internet) via network adapter 550. As depicted, network adapter 550 communicates with the other components of computer system/server 502 via bus 515. It should be understood that although not shown, other hardware and/or software components could be used in conjunction with computer system/server 502. Examples include, but are not limited to: microcode, device drivers, redundant processing units, external disk drive arrays, RAID systems, tape drives, and data archival storage systems, etc.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 6:
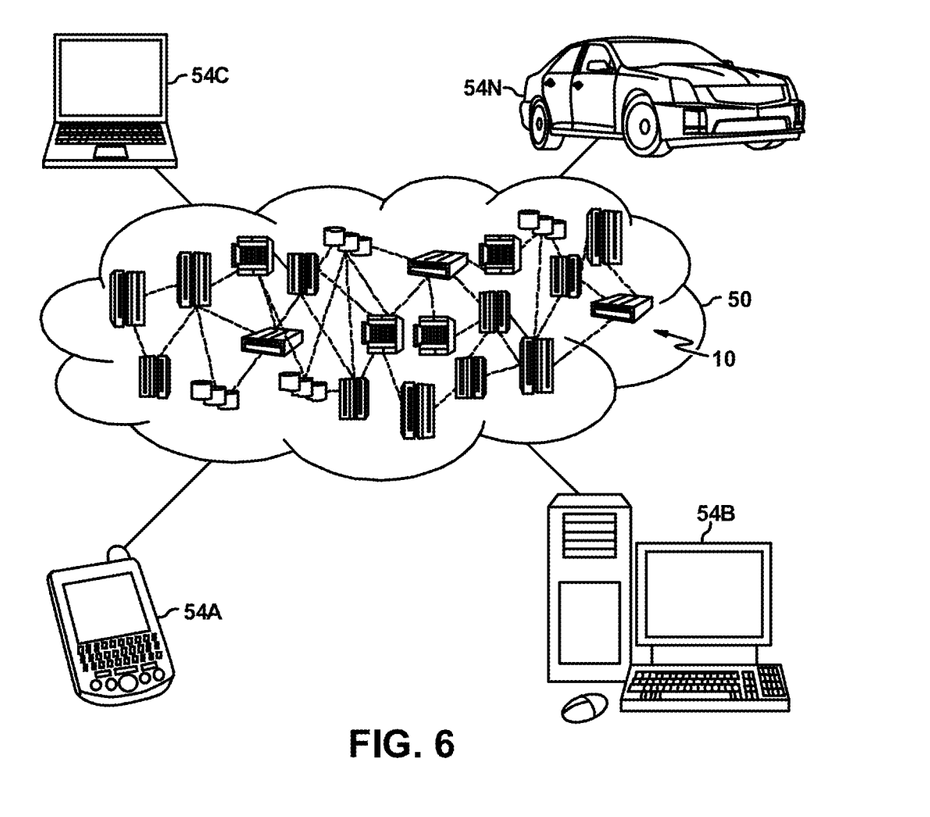
FIG. 6 depicts a cloud computing environment, according to some embodiments.

Referring now to FIG. 6, illustrative cloud computing environment 50 is depicted, according to some embodiments. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 6 are intended to be illustrative only and that computing nodes 10 and cloud computing environment 50 can communicate with any type of computerized device over any type of network and/or network addressable connection (e.g., using a web browser).

Figure 7:
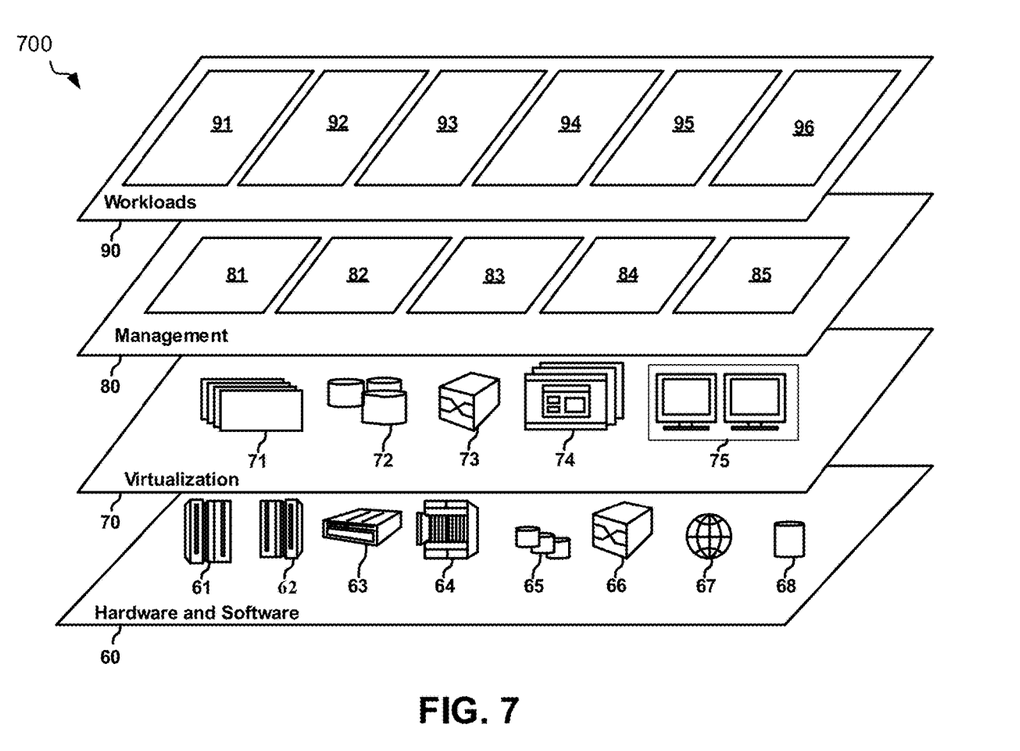
FIG. 7 depicts abstraction model layers, according to some embodiments.

Referring now to FIG. 7, a set of functional abstraction layers 700 provided by cloud computing environment 50 (FIG. 6) is shown, according to some embodiments. It should be understood in advance that the components, layers, and functions shown in FIG. 7 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture-based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below.

Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and ping-pong processing 96.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electronic signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object orientated program language such as Smalltalk, C++, or the like, and procedural programming languages, such as the "C" programming language or similar programming languages. The computer readable program instructions may execute entirely one the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to some embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present disclosure have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method comprising:
   determining whether a user is awaiting a first notification on a mobile device;
   estimating an anxiety level of the user based on the determining, wherein the awaiting the first electronic notification results in a higher estimated anxiety level of the user than if the user was not awaiting the first electronic notification;
   determining whether the anxiety level is above a threshold anxiety level;
   calculating, in response to determining that the anxiety level is above the threshold anxiety level, a ping-pong rate for the mobile device; and
   reducing the ping-pong rate.

2. The method of claim 1, wherein the determining whether the user is awaiting the first notification comprises:
   parsing an information flow across one or more applications on the mobile device;
   building context of user communications based on the parsing; and
   estimating, based on the building, whether any notifications are expected to be received by the mobile device in an impending time period.

3. The method of claim 2, wherein the one or more applications include at least one of a messaging application, an email application, and a calendar application.

4. The method of claim 1, wherein the mobile device is connected to one or more health devices.

5. The method of claim 4, wherein estimating an anxiety level of the user comprises:
   collecting health data from the one or more health devices;
   analyzing the health data from the one or more health devices; and
   determining, based on the analyzing, an approximation of the anxiety level of the user.

6. The method of claim 5, wherein determining whether the anxiety level is above the threshold anxiety level comprises:
   collecting past health data from the one or more health devices in a past time period;
   determining, using the past health data, a threshold health level of the user;
   determining the threshold anxiety level of the user using the threshold health level; and
   comparing the anxiety level to the threshold anxiety level.

7. The method of claim 1, wherein reducing the ping-pong rate comprises:
   determining that a cell tower connected to the mobile device has a signal strength greater than a threshold strength; and
   decreasing, in response to the determining that the cell tower has the signal strength greater than the threshold strength, a power of electromagnetic frequency emissions transmitted from the mobile device.

8. The method of claim 1, further comprising:
   disabling a vibration alert mechanism for any incoming notifications but the first notification.

9. The method of claim 8, further comprising:
   receiving the first notification; and
   reinstating, in response to the receiving, the vibration alert mechanism for all notifications.

10. The method of claim 1, further comprising:
    locking applications that are not relevant to the first notification.

11. The method of claim 1, further comprising:
    displaying a prompt suggesting that the user change an orientation of the mobile device.

12. A system having one or more computer processors, the system configured to:
    determine whether a user is awaiting a first notification on a mobile device;
    estimate an anxiety level of the user based on the determining, wherein the awaiting the first electronic notification results in a higher estimated anxiety level of the user than if the user was not awaiting the first electronic notification;
    determine whether the anxiety level is above a threshold anxiety level;
    calculate, in response to determining that the anxiety level is above the threshold anxiety level, a ping-pong rate for the mobile device; and
    reduce the ping-pong rate.

13. The system of claim 12, wherein the determining whether the user is awaiting the first notification comprises:
    parsing an information flow across one or more applications on the mobile device;
    building context of user communications based on the parsing; and
    estimating, based on the building, whether any notifications are expected to be received by the mobile device in an impending time period.

14. The system of claim 12, wherein the mobile device is connected to one or more health devices.

15. The system of claim 14, wherein estimating an anxiety level of the user comprises:
    collecting health data from the one or more health devices;
    analyzing the health data from the one or more health devices; and
    determining, based on the analyzing, an approximation of the anxiety level of the user.

16. The system of claim 15, wherein determining whether the anxiety level is above the threshold anxiety level comprises:
    collecting past health data from the one or more health devices in a past time period;
    determining, using the past health data, a threshold health level of the user;
    determining the threshold anxiety level of the user using the threshold health level; and
    comparing the anxiety level to the threshold anxiety level.

17. A computer program product comprising a computer readable storage medium having program instructions embodied therewith, the program instructions executable by a server to cause the server to perform a method, the method comprising:

determining whether a user is awaiting a first notification on a mobile device;

estimating an anxiety level of the user based on the determining, wherein the awaiting the first electronic notification results in a higher estimated anxiety level of the user than if the user was not awaiting the first electronic notification;

determining whether the anxiety level is above a threshold anxiety level;

calculating, in response to determining that the anxiety level is above the threshold anxiety level, a ping-pong rate for the mobile device; and reducing the ping-pong rate.

18. The computer program product of claim 17, wherein the determining whether the user is awaiting the first notification comprises:

parsing an information flow across one or more applications on the mobile device;

building context of user communications based on the parsing; and estimating, based on the building, whether any notifications are expected to be received by the mobile device in an impending time period.

19. The computer program product of claim 17, wherein the mobile device is connected to one or more health devices, and wherein estimating an anxiety level of the user comprises:

collecting health data from the one or more health devices;

analyzing the health data from the one or more health devices; and determining, based on the analyzing, an approximation of the anxiety level of the user.

20. The computer program product of claim 19, wherein determining whether the anxiety level is above the threshold anxiety level comprises:

collecting past health data from the one or more health devices in a past time period;

determining, using the past health data, a threshold health level of the user;

determining the threshold anxiety level of the user using the threshold health level; and comparing the anxiety level to the threshold anxiety level.

* * * * *